(12) United States Patent
Thorpe et al.

(10) Patent No.: US 7,625,733 B2
(45) Date of Patent: Dec. 1, 2009

(54) ISOLATION OF QUIESCIN-SULFHYDRYL OXIDASE FROM MILK

(75) Inventors: Colin Thorpe, Newark, DE (US); Jennifer Jaje, Newark, DE (US)

(73) Assignee: University of Delaware, Newark, DE (US)

( * ) Notice: Subject to any disclaimer, the term of this patent is extended or adjusted under 35 U.S.C. 154(b) by 0 days.

(21) Appl. No.: 12/220,464

(22) Filed: Jul. 24, 2008

(65) Prior Publication Data

US 2009/0042269 A1    Feb. 12, 2009

Related U.S. Application Data

(60) Provisional application No. 60/963,060, filed on Aug. 2, 2007.

(51) Int. Cl.
*C12N 9/02* (2006.01)
*A23J 1/00* (2006.01)

(52) U.S. Cl. ........................... 435/189; 530/412

(58) Field of Classification Search ................. 435/189; 530/412

See application file for complete search history.

(56) References Cited

U.S. PATENT DOCUMENTS 6,075,008 A    6/2000    Farrell et al.

OTHER PUBLICATIONS

Raje, Sonali, Glynn, Nicole M., Thorpe; "A continuous fluorescence assay for sulfhydryl oxidase," Analytical Biochemistry, vol. 307; Aug. 15, 2002; pp. 266-272.
Isaacs, Charles E. et al.; "Sulfhydryl Oxidase in Human Milk: Stability of Milk Enzymes in the Gastrointestinal Tract," Pediatric Research, vol. 18, No. 6; 1984; pp. 532-535.
Coppock, Donald L. and Thorpe, Colin; "Multidomain Flavin-Dependent Sulfhydryl Oxidases," Antioxidants & Redox Signaling, vol. 8, Nos. 3 & 4; 2006; pp. 300-311.
Thorpe, Colin and Coppock, Donnald L.; "Generating disulfides in multicellular organisms: emerging roles for a new flavoprotein family," The Journal of Biological Chemistry; Mar. 12, 2007; pp. 1-14.
Kusakabe, Hitoshi, Kuninaka, Akira and Yoshino, Hiroshi; "Purification and Properties of a New Enzyme, Glutathione Oxidase from Penicillium sp. K-6-5," Agric. biol. Chem., vol. 46, No. 8; 1982; pp. 2057-2067.
Hoober, Karen L. et al.; "Homology between Egg White Sulfhydryl Oxidase and Quiescin Q6 Defines a New Class of Flavin-linked Sulfhydryl Oxidases," The Journal of Biological Chemistry, vol. 274, No. 45; Nov. 5, 1999; pp. 31759-31762.
Janolino, Violeta G. and Swaisgood, Harold E.; "Isolation and Characterization of Sulfhydryl Oxidase from Bovine Milk," The Journal of Biological Chemistry, vol. 250, No. 7; Apr. 10, 1975; pp. 2532-2538.

Swaisgood, Harold E. and Janolino, Violeta G.; "Mammalian Sulfhydryl Oxidase," Handbook of Food Enzymology; Marvel Delkar 2003; pp. 539-546.
Hoober, Karen L. et al.; "Sulfhydryl Oxidase from Egg White," The Journal of Biological Chemistry, vol. 274, No. 32; Aug. 6, 1999; pp. 22147-22150.
Thorpe, Colin et al.; "Sulfhydryl oxidases: emerging catalysts of protein disulfide bond formation in eukaryotes," Archives of Biochemistry and Biophysics, vol. 405; 2002; pp. 1-12.
De La Motte, Rebecca S. and Wagner, Fred W.; "*Aspergillus niger* Sulfhydryl Oxidase," Biochemistry, vol. 26; 1987; pp. 7363-7371.
Janolino, Violeta and Swaisgood, H.E.; "A comparison of sulfydryl oxidases from bovine milk and from *Aspergillus niger*," Milchwissenschaft, vol. 47, No. 3; 1992; pp. 143-146.
Hoober, Karen L. et al.; "A Sulfydryl Oxidase from Chicken Egg White," The Journal of Biological Chemistry, vol. 271, No. 48; Nov. 29, 1996; pp. 30510-30516.
Parmentier, Kathryn; "Determination of the Volume of Industrial Waste from Wisconsin's Dairy Products Industry", University of Wiaconsin—Green Bay, May 9, 2000.
Smithers, Geoffrey W. et al.; "New Opportunities from the Isolation and Utilization of Whey Proteins," Journal of Dairy Science, vol. 79; 1996; pp. 1454-1459.
Etzel, Mark R.; "Manufacture and Use of Dairy Protein Fractions," American Society for Nutritional Sciences; 2004; pp. 996S-1002S.
Jaje, Jennifer et al.; "A Flavin-Dependent Sulfhydryl Oxidase in Bovine Milk," Biochemistry, vol. 46; 2007; pp. 13031-13040.
Hoober, Karen L. and Thorpe, Colin; "Flavin-Dependent Sulfhydryl Oxidases in Protein Disulfide Bond Formation," Methods in Enzymology, vol. 348; 2002; pp. 30-34.
Hoober, Karen L. and Thorpe, Colin; "Egg White Sulfydryl Oxidase: Kinetic Mechanism of the Catalysis of Disulfide Bond Formation," Biochemistry, vol. 38, No. 10; 1999; pp. 3211-3217.
Sliwkowski, Mary B., Swaisgood, Harold E. and Horton, Robert; "Solubilization of Sulfhydryl Oxidase, A Bovine Skim Milk Membrane Enzyme," Journal of Dairy Science, vol. 65; 1982; pp. 1681-1687.
Coppock, Donald L. et al.; "Preferential Gene Expression in Quiescent Human Lung Fibroblasts," Cell Growth and Differentiation, vol. 4; Jun. 1993; pp. 483-493.
*Cheese: Chemistry, Physics and Microbiology*, Third Eddition, vol. 1; Elsevier Academic Press; 2004.
*Ion Exchange Chromatography & Chromatofocusing: Principles and Methods*; Amersham Biosciences; 2004.
*Hydrophobic Interaction and Reversed Phase Chromatography: Principles and Methods*; GE Healthcare; 2006.

*Primary Examiner*—Tekchand Saidha
(74) *Attorney, Agent, or Firm*—RatnerPrestia

(57) ABSTRACT

Methods for isolating a highly purified QSOX enzyme from milk or whey are described. The enzyme may be used to generate intermolecular and intramolecular disulfide bridges and to facilitate oxidative protein folding.

19 Claims, 3 Drawing Sheets

UV/Vis spectrum of purified milk sulfhydryl oxidase.

SEQUENCE LISTING

<160> NUMBER OF SEQ ID NOS: 1

<210> SEQ ID NO 1
<211> LENGTH: 521
<212> TYPE: PRT
<213> ORGANISM: Bos taurus

-continued

<400> SEQUENCE: 1

```
Ser Ala Leu Tyr Ser Ser Ser Asp Pro Leu Thr Leu Leu Arg Ala Asp
1               5                   10                  15

Thr Val Arg Ser Thr Val Leu Gly Ser Ser Ala Trp Ala Val Glu
            20                  25                  30

Phe Phe Ala Ser Trp Cys Gly His Cys Ile Ala Phe Ala Pro Thr Trp
                35                  40                  45

Lys Ala Leu Ala Asn Asp Val Lys Asp Trp Arg Pro Ala Leu Asn Leu
    50                  55                  60

Ala Ala Leu Asp Cys Ala Glu Glu Thr Asn Ser Ala Val Cys Arg Asp
65                  70                  75                  80

Phe Asn Ile Pro Gly Phe Pro Thr Val Arg Phe Phe Lys Ala Phe Ser
                85                  90                  95

Lys Thr Gly Ser Gly Thr Thr Leu Ser Val Ala Gly Ala Asp Val Gln
                100                 105                 110

Thr Leu Arg Glu Arg Leu Ile Asp Ala Leu Glu Ser His Ser Asp Thr
            115                 120                 125

Trp Pro Pro Ala Cys Pro Pro Leu Glu Pro Ala Arg Leu Glu Glu Ile
130                 135                 140

Thr Gly Phe Phe Ala Arg Asn Asn Glu Glu Tyr Leu Ala Leu Ile Phe
145                 150                 155                 160

Glu Lys Glu Gly Ser Tyr Leu Gly Arg Glu Val Thr Leu Asp Leu Ser
                165                 170                 175

Gln His Gln Gly Ile Ala Val Arg Arg Val Leu Asn Thr Glu Arg Asp
            180                 185                 190

Val Val Asn Arg Phe Gly Val Thr Asn Phe Pro Ser Cys Tyr Leu Leu
        195                 200                 205

Ser Arg Asn Gly Ser Phe Ser Arg Val Pro Ala Leu Thr Glu Ser Arg
    210                 215                 220

Ser Phe Tyr Thr Thr Tyr Leu Arg Lys Phe Ser Gly Ser Thr Arg Gly
225                 230                 235                 240

Ala Val Gln Thr Thr Ala Ala Pro Ala Thr Thr Ser Ala Val Ala Pro
                245                 250                 255

Thr Val Trp Lys Val Ala Asp Arg Ser Lys Ile Tyr Met Ala Asp Leu
            260                 265                 270

Glu Ser Ala Leu His Tyr Ile Leu Arg Ile Glu Val Gly Lys Phe Ser
        275                 280                 285

Val Leu Glu Gly Gln Arg Leu Val Ala Leu Lys Lys Phe Met Ala Val
    290                 295                 300

Leu Ala Lys Tyr Phe Arg Gly Arg Pro Leu Val Gln Asn Phe Leu His
305                 310                 315                 320

Ser Met Asn Asp Trp Leu Lys Lys Gln Gln Arg Lys Lys Ile Pro Tyr
                325                 330                 335

Gly Phe Phe Lys Asn Ala Leu Asp Ser Arg Lys Glu Gly Thr Val Ile
            340                 345                 350

Ala Glu Lys Val Asn Trp Val Gly Cys Gln Gly Ser Glu Pro His Phe
        355                 360                 365

Arg Gly Phe Pro Cys Ser Leu Trp Ile Leu Phe His Phe Leu Thr Val
    370                 375                 380

Gln Ala Ala Gln Glu Gly Val Asp His Pro Gln Glu Arg Ala Lys Ala
385                 390                 395                 400

Gln Glu Val Leu Gln Ala Ile Arg Gly Tyr Val Arg Phe Phe Phe Gly
                405                 410                 415
```

-continued

```
Cys Arg Glu Cys Ala Gly His Phe Glu Gln Met Ala Ser Gly Ser Met
            420                 425                 430

His Arg Val Gly Ser Leu Asn Ser Ala Val Leu Trp Phe Trp Ser Ser
        435                 440                 445

His Asn Lys Val Asn Ala Arg Leu Ala Gly Ala Pro Ser Glu Asp Pro
    450                 455                 460

Gln Phe Pro Lys Val Gln Trp Pro Pro Arg Glu Leu Cys Ser Ala Cys
465                 470                 475                 480

His Asn Glu Leu Arg Gly Thr Pro Val Trp Asp Leu Asp Asn Ile Leu
            485                 490                 495

Lys Phe Leu Lys Thr His Phe Ser Pro Ser Asn Ile Val Leu Asp Phe
            500                 505                 510

Pro Ser Ala Gly Pro Gly Pro Trp Arg
            515                 520
```

ISOLATION OF QUIESCIN-SULFHYDRYL OXIDASE FROM MILK

This application claims benefit of priority from provisional application US 60/963,060, filed on Aug. 2, 2007, incorporated herein by reference.

REFERENCE TO U.S. GOVERNMENT SUPPORT AND RELATED APPLICATIONS

This invention was made with Government support under NIH GM 26643, awarded by the National Institutes of Health. The Government has certain rights in this invention.

BACKGROUND OF THE INVENTION

Quiescin sulfhydryl oxidases (QSOX) are flavin-dependent enzymes that catalyze the oxidation of sulfhydryl groups to disulfides with reduction of oxygen to hydrogen peroxide. They were originally associated with quiescence in fibroblasts, and were later shown to have sulfhydryl oxidase activity. The QSOX family of enzymes is formed from the fusion of thioredoxin domains and FAD-binding domains (ERV1/ALR). QSOX genes have been identified in all multicellular plants and animals and in some protista, but have not been found in fungi. (Reviewed in D. Coppock and C. Thorpe, *Antioxidants & Redox Signalling* 8: 300-311, 2006; C. Thorpe and D. Coppock, *J. Biol. Chem.* 282: 13929-13933, 2007).

The QSOX enzymes are distinct from fungal sulfhydryl oxidases, which are actually glutathione oxidases (H. Kusakabe, et al., *Agric. Biol. Chem.* 46: 2057-2067, 1982; K. Hoober et al., *J. Biol. Chem.* 274: 31759-31761, 1999) and the metal-dependent sulfhydryl oxidase reported by V. G. Janolino and H. E. Swaisgood, *J. Biol. Chem.* 250: 2532-2538, 1975; *Food Science and Technology* 122: 539-546, 2003. QSOX enzymes exhibit much greater activity in protein-cysteine oxidation than fungal glutathione oxidases (K. Hoober et al., *J. Biol. Chem.* 274: 22147-22150, 1999; C. Thorpe, et al., *Arch. Biochem. Biophys.* 405: 1-12, 2002).

Kusakabe et al. have shown that the sulfhydryl oxidase from *Penicillium* sp. has undetectable activity in introducing disulfides into protein substrates, using standard assays employing RNAse as a standard protein for oxidative protein folding studies. H. Kusakabe, et al., *Agric. Biol. Chem.* 46: 2057-2067, 1982.

Similarly, de la Motte and Wagner, as well as Janolino and Swaisgood, using RNAse as a substrate, have shown that the *Aspergillus* sulfhydryl oxidase has extremely low activity (less than 0.02 thiols oxidized per minute). R. S. de la Motte and F. W. Wagner, *Biochemistry* 26: 7363-7371, 1987; V. G. Janolino and H. E. Swaisgood, *Milchwissenschaft* 47: 143-146, 1992.

A comparison of the distinctive properties of QSOX1 (quiescin Q6 sulfhydryl oxidase 1) and metal-dependent sulfhydryl oxidase from milk (MetalSox) is shown in Table 1.

TABLE 1

Comparison of the properties of purified QSOX1 from milk and reported metal-dependent sulfhydryl oxidase from milk

| Property | Milk-QSOX1 | MetalSOX |
| --- | --- | --- |
| Molecular weight | 62 kDa | 89 kDa |
| Cofactor content | Flavin (FAD) | Iron (Fe) |
| Is activity stimulated by added Ferrous iron? | No | Yes |
| Is EDTA inhibitory? | No | Yes |
| Sequence information Available? | Yes | No |
| Catalytic efficiency with reduced RNase ($kcat/Km$ ($M^{-1}s^{-1}$)) per thiol | $3.74 \times 10^5$ | Not available in the literature |

A QSOX enzyme isolated from human placental tissue has also been shown to have activity in stimulating cell proliferation and growth in normal and cancer cells, as described in U.S. Pat. No. 6,075,008 (SEQ ID NOs: 4 and 6), and may have therapeutic uses.

Avian QSOX1 can be isolated from egg white, which yields approximately 0.4 mg QSOX1 per 100 g of egg white protein (Hoober et al., *J. Biol. Chem.* 271, 30510-30516, 1996). However, the high viscosity of egg white makes isolation and purification of QSOX1 from this source very difficult. Human QSOX1 has been localized in a number of human tissues by immunohistochemistry, but is present only in very small amounts in these tissues (Coppock and Thorpe, *Antioxidants & Redox Signalling* 8: 300-311, 2006).

Whey is a liquid by-product from the preparation of cheese or casein from cow's milk. For every pound of cheese produced, approximately 9 pounds of liquid whey result. It has been estimated that dairies in the state of Wisconsin alone produce about 19 billion pounds of liquid whey byproduct annually from cheese production, which incurs substantial costs in disposal and waste management. (K. Parmentier, Determination of the Volume of Industrial Waste from Wisconsin's Dairy Products Industry, www.wastenot-organics.wisc.edu/library/whey). In 1996, it was reported that worldwide, volumes of whey accumulated at greater than $80 \times 10^9$ liters per year (G. W. Smithers, et al., *J. Dairy Sci.* 79: 1454-1459, 1996). Whey has some limited commercial uses as an additive in processed foods and animal feed, as a nutritional supplement, and as a commercial source of lactoferrin and lactoperoxidase. (G. W. Smithers, et al., *J. Dairy Sci.* 79: 1454-1459, 1996; M. R. Etzel, *J. Nutrition.* 134, 996S-1002S, 2004).

Quiescin sulfhydryl oxidases (QSOX) are useful in generating disulfide bonds in small molecules, and in unfolded, reduced peptides and proteins, thereby facilitating protein folding, and in generating intermolecular and intramolecular disulfide bonds, for example, in the formation of disulfide-bridged networks and gels. QSOX enzymes use only oxygen as an oxidant and are the most versatile disulfide bond-forming enzymes yet known. In addition, they may also be used as enzymatic oxidants for sulfhydryl compounds in aqueous solution in the presence of molecular oxygen, and as an alternative to chemical oxidants in the re-oxidation of hair and wool fibers, or of other materials reduced with suitable reductants. Although other sulfhydryl oxidases have been reported, only QSOX enzymes have been shown to readily insert disulfide bonds into a wide range of sulfhydryl compounds, in particular, peptides and proteins. (K. L. Hoober et al., *J. Biol. Chem.* 274: 22147-22150, 1999; C. Thorpe and D. L. Coppock, *J. Biol. Chem.* 282: 13923-13933, 2007). Due to the superior performance of QSOX enzymes in creating disulfide bonds and mediating oxidative protein folding, a need exists for a cost-effective method to provide these enzymes commercially.

Despite these important industrial and medical uses, there is currently no known purification procedure of any QSOX enzyme that could be adapted for industrial scale purification of QSOX proteins, in part because no feasible source of QSOX for industrial purification has been found.

SUMMARY OF THE INVENTION

An isolated and purified QSOX polypeptide having at least 95% identity to the amino acid sequence of SEQ ID NO:1 is described, wherein the isolated and purified polypeptide is capable of inserting a disulfide bond into a polypeptide.

One aspect of the invention is a method for isolating a QSOX polypeptide in high purity from milk comprising the steps of preparing a solution of whey from the milk, acidifying the solution of whey, applying the acidified solution of whey to a cation exchanger, eluting and identifying fractions containing quiescin sulfhydryl oxidase from the cation exchanger, and further purifying quiescin sulfhydryl oxidase in the eluted fractions.

Another aspect of the invention comprises a method for isolating and partially purifying a QSOX polypeptide from a solution of whey comprising the steps of acidifying the solution of whey, applying the acidified solution of whey to a cation exchanger, eluting and identifying fractions containing quiescin sulfhydryl oxidase from the cation exchanger, and further purifying quiescin sulfhydryl oxidase in the eluted fractions.

DETAILED DESCRIPTION OF THE INVENTION

Figure 1:
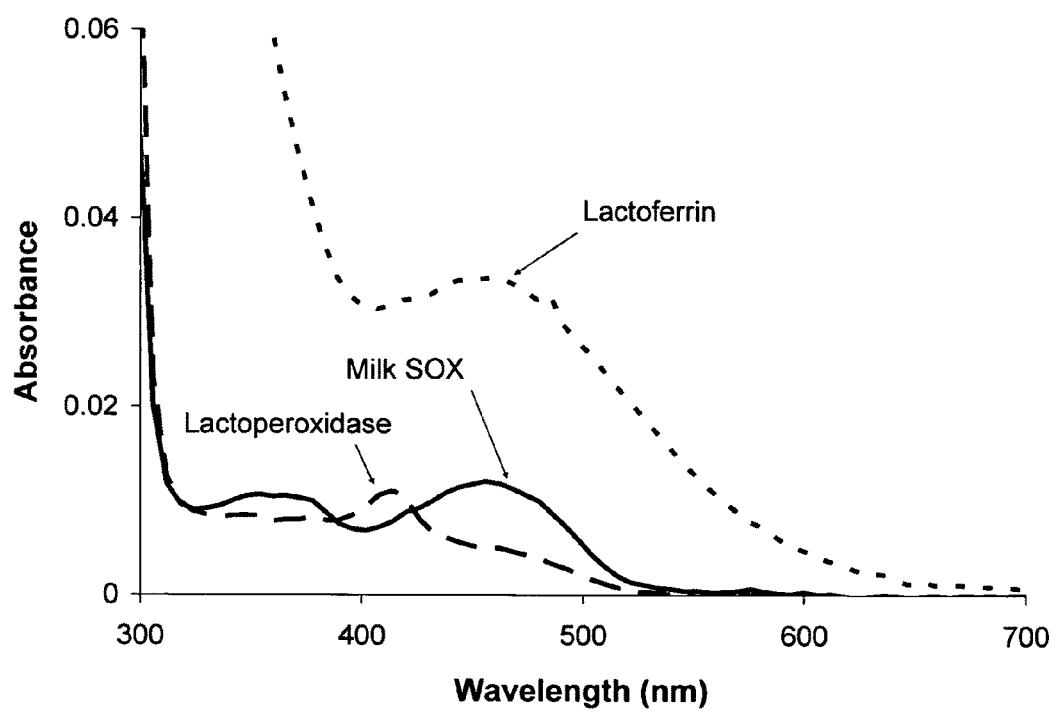
FIG. 1 shows the visible spectra of three species eluting from a butyl-Sepharose hydrophobic interaction chromatography column.

As described below, the present invention demonstrates that milk is a convenient and significant source of QSOX1, and methods are introduced to isolate and purify commercially feasible quantities of active QSOX1 from milk and whey. The studies on milk QSOX1 are further described in Jaje, et al., *Biochemistry* 46: 13031-13040, 2007, and accompanying supplemental information at pubs.acs.org, which are incorporated herein by reference in their entirety. It has been demonstrated through this invention that QSOX1 is present in bovine milk and can be extracted and purified from whey in commercially feasible quantities (at least, approximately 3.3 mg QSOX1 per 100 g whey protein) using ion-exchange and hydrophobic interaction chromatography. In addition, because milk and whey solutions are comparatively non-viscous, QSOX1 is more easily isolated and purified from milk and whey than from egg white.

Bovine QSOX1 isolated from milk is a flavin-dependent sulfhydryl oxidase. Some properties of bovine QSOX1 are shown above in Table 1, and the amino acid sequence of mature bovine QSOX1 is given in SEQ ID NO:1. Bovine QSOX1 from milk can be used to insert disulfide bonds into a wide variety of substrates, including reduced, unfolded proteins and thiol-containing networks and gels. Bovine QSOX1 catalyzes the oxidation of a test reduced protein, e.g., pancreatic RNase, with a catalytic efficiency two-fold higher than the egg white QSOX1, as shown in Table 2 of Example 3, below. This latter protein has been shown to catalyze the oxidation of a wide range of reduced proteins and peptides (Hoober et al., *J. Biol. Chem.* 274:22147-22150).

Although bovine milk is a preferred source of QSOX1, sulfhydryl oxidase activity has also been found in small amounts in human, rabbit, and rat milk (C. E. Isaacs, et al., *Pediatric Research* 18: 532-535, 1984). As secreted QSOX1 is expected to be a general feature of milk, the enzyme may also be present in commercially feasible quantities in the milk of other animals, such as sheep and goats. Accordingly, the invention described herein is not limited to bovine milk.

Whey is a by-product of cheese-making and can be readily obtained in large volumes from the dairy industry. Whey solution can be created by the well-known procedures of precipitating casein by acidifying milk or adding rennet/chymosin to milk, as described, for example, in Cheese: *Chemistry, Physics and Microbiology, Volume 1, Third Edition: General Aspects*, Patrick F. Fox, Paul McSweeney, Timothy Cogan, Timothy Guinee, Eds. Academic Press, 2004.

QSOX1 can be isolated and purified from whey in the laboratory using an ammonium sulfate precipitation in combination with ion-exchange chromatography and hydrophobic interaction chromatography, as described in Example 1. On an industrial scale, QSOX1 may be isolated and purified from cow's milk using high performance ion-exchange resins. Similar methods are currently used commercially to isolate lactoferrin and lactoperoxidase from milk and whey.

Beginning with whey, a whey protein concentrate may be prepared by ultrafiltration or diafiltration as known to those of skill in the art (P. Hobman, in *Whey and Lactose Processing*. Elsevier: New York, 1992, pp. 195-230; R. Baker, *Membrane technology and applications*, Wiley: New York, 2004; A. Shukla, et al. *Process scale bioseparations for the biopharmaceutical industry* CRC: Boca Raton, 2007). The solution may then be adjusted to an appropriate pH, e.g. 4.5-8.0, and applied to a cation-exchange absorbent material. The cation-exchange material may include, but is not limited to, carboxymethyl cellulose; sulfopropylcellulose; TosoHaas Toyopearl SP, CM and HW; EMD sulfonate and carboxylate; BioSepra SP and CM; GE Healthcare SP Sepharose Fast Flow/Big Beads; CM Sepharose Fast Flow; and CM Spherosil. The cation exchange material may be used in the form of a column, in conventional or expanded bed adsorption formats, or in a batch mode (e.g., as described in R. Pearce, *Whey and Lactose Processing*. Elsevier: New York, 1992, pp. 271-316; A. Ahuja, *Handbook of Bioseparations*. Separation Science and Technology, Academic Press: New York, 2000). The amount of absorbent material selected will depend on the volume of whey solution to be applied.

By way of example, when a column format is utilized, the cation-exchange column is washed with a buffered solvent, which may include one or more cations, such as ammonium, calcium, sodium, potassium, and protonated tris(hydroxymethyl)aminomethane; and one or more compatible anions, such as acetate, chloride, citrate, phosphate, pyrophosphate, succinate, and sulfate. The column is then eluted with buffered solvent containing increasing gradients of a solution that may include one or more cations, such as ammonium, calcium, sodium, potassium, and protonated tris(hydroxymethyl)aminomethane and one or more anions, such as acetate, chloride, citrate, phosphate, pyrophosphate, succinate, and sulfate, up to an aggregate ionic strength of 2.0 M. Those of skill in the art will understand how to select optimal buffers and buffer concentrations for washing and elution, for example, as described in Ion Exchange Chromatography &

Chromatofocusing: Principles and Methods, GE Healthcare www4.gelifesciences.com/aptrix/upp00919.nsf/Content/ 71857706466D1AB8C1256EB 40041805D/$file/ 11000421AA.pdf (2004).

Ion-exchange chromatography may also be conducted as a batch process or by conventional or expanded bed chromatographies, as described, for example, in R. Pearce, in *Whey and Lactose Processing*. Elsevier: New York, 1992, pp. 271-316; and A. Ahuja, *Handbook of Bioseparations*. Separation Science and Technology. Academic Press: New York, 2000.

Eluted fractions containing QSOX1 can be identified by enzyme assays (K. L. Hoober, et al., *J. Biol. Chem.* 271: 30510-30516, 1996; K. L. Hoober, et al., *J. Biol. Chem.* 274: 22147-22150, 1999; K. L. Hoober and C. Thorpe, *Methods Enzymol.* 348: 30-34, 2002); by following the oxidation of substrate sulfhydryl groups using 5, 5'-dithiobis-(2-nitrobenzoic acid) (K. L. Hoober, et al., *J. Biol. Chem.* 274: 22147-22150, 1999; K. L. Hoober and C. Thorpe, *Methods Enzymol.* 348: 30-34, 2002); by monitoring the production of hydrogen peroxide (S. Raje, et al., *Anal Biochem* 307(2): 266-272, 2002); or by using the visible spectrum of the bound flavin as depicted in FIG. 1 and as exemplified in Example 1 and in K. L Hoober, et al., *J. Biol. Chem.* 271: 30510-30516, 1996.

Fractions containing QSOX1 can be combined and further purified by one or more of the following standard protein separation techniques. Hydrophobic interaction chromatography is typically performed by bringing the protein solution to 40% saturation with ammonium sulfate and adsorbing the solution to the contents of a chromatography column containing a suitable adsorbent (e.g., including, but not limited to, Butyl Sepharose FF, Phenyl Sepharose FF HS, TSK-gel-Phenyl-5PW, Toyopearl Phenyl 650, Toyopearl Butyl 650, Toyopearl Hexyl 650, Phenyl Sepharose HP, Fractogel EMD phenyl, Source 15PHE or POROS 20 HP2). Those skilled in the art will know how to vary parameters to maximize the yield and purification obtained by hydrophobic interaction chromatography, including the gradient of ammonium sulfate, the buffer composition (see buffers used for the ion-exchange separation listed above), and the temperature of elution. Hydrophobic Interaction and Reversed Phase Chromatography Principles and Methods. GE Healthcare (www4.gelifesciences.com/aptrix/upp00919.nsf/Content/ C5EDE7D9A195E1DBC1257124000DD446/$file/ 11001269AA.pdf) (2006). The concentration of sulfhydryl oxidase in the eluates can be established using one or more of the assays described above for detecting fractions containing QSOX1.

Alternative (or supplementary) purification methods include, but are not limited to, an additional chromatographic step; repeating the ion exchange separation under different conditions of stationary phase (e.g., from the list of ion exchange resins listed above), and/or mobile phase (buffer, gradient, pH and temperature) to resolve impurities (as described in detail in Example 1); or using size exclusion chromatography as described, for example, in C. Wu, *Handbook of size exclusion chromatography and related techniques*. Marcel Dekker: New York, 2004, in a compatible buffer such as those mentioned above for the ion exchange step. Through the use of successive purification steps, it is possible to produce QSOX1 that is at least 90% pure.

Isolated and purified QSOX1 from cow's milk has the amino acid sequence listed in SEQ ID NO:1 and is characterized as described below in Examples 2 and 3. Functional variants of the polypeptide having an amino acid sequence which has at least 95% identity to SEQ ID NO:1 are also encompassed by the invention. A functional variant is a polypeptide having substantially the same enzymatic activity as the polypeptide of SEQ ID NO:1. Enzymatic activity may be determined by any method known in the art, for example as described below in Example 3. Preferred variants will have conservative amino acid substitutions.

Functional variants of the polypeptide of SEQ ID NO:1 may be genetically engineered by any appropriate method known in the art, for example, as described in standard laboratory manuals such as Sambrook, et al., *Molecular Cloning: A Laboratory Manual*, $2^{nd}$ Ed., Cold Spring Harbor Laboratory Press, Cold Spring Harbor, N.Y. (1989) and *Current Protocols in Molecular Biology*, F. M. Ausubel, et al., Eds., John Wiley & Sons (2008); or may result from mutation in vivo. Percent identity to SEQ ID NO:1 is determined by multiplying the total number of amino acids in SEQ ID NO:2 by the integer defining the percent identity divided by 100 and then subtracting that product from the total number of amino acids in SEQ ID NO:1. For example, SEQ ID NO:1 contains 521 amino acids; 521−(521−0.95)=521−495=26; therefore a variant having at least 95% identity to SEQ ID NO:1 has 26 or fewer differences in amino acid sequence compared with SEQ ID NO:1.

EXAMPLES

1. Isolation of QSOX1 from Cow's Milk

Whey was prepared by adding about 190 ml of 1 M HCl to about 3.4 liters of skim milk (final pH 4.6), and then centrifuging the mixture at 4200 g for 15 min at 4° C. to precipitate casein. The whey supernatant was neutralized to pH 7.4 with 1 M KOH, then EDTA (to 1 mM) and a protease inhibitor cocktail tablet (Roche, Indianapolis, Ind., USA) was added to the stirred solution. The solution was brought to 65% saturation in ammonium sulfate and left at 4° C. to settle overnight. The precipitate was recovered by centrifugation and one-half was resuspended in 20 mM phosphate buffer, pH 6.0, containing 1 mM EDTA (following the purification outlined below, the remaining half could be so treated).

The suspension was dialysed against two 4 h changes of 1 L buffer and then overnight against 1 L of buffer supplemented with a protease inhibitor tablet. Stirring was then stopped and a precipitate allowed to settle to the bottom of the dialysis tubing. The supernatants were centrifuged at 2600 g for 20 min to remove any remaining precipitate, and the straw-colored supernatant was collected and applied to a 5×24 cm CM52 cation exchange column (Whatman, Brentford, Middlesex, U.K.), which was previously equilibrated in 20 mM phosphate buffer containing 1 mM EDTA. The column was developed with a gradient of KCL as follows: the low-salt reservoir (the 20 mM buffer) supplied the head of the column at 156 mL/hour and was replenished at the same flow rate with a solution of 1 M KCl dissolved in the same buffer. Fractions were collected at six minute intervals and analyzed by UV/VIS spectra. Small aliquots from each fraction were screened for sulfhydryl oxidase and peroxidase activity in a 96-well plate.

Fractions containing significant sulfhydryl oxidase activity were pooled, brought to 40% ammonium sulfate and then applied at 1 ml/min to a butyl-Sepharose column (2.5×7.5 cm) (resin from GE Healthcare, Piscataway, N.J.) previously equilibrated at room temperature with 40% ammonium sulfate in 20 mM phosphate buffer, pH 7.5, containing 1 mM EDTA. The top of the column was supplied at 1 ml/min from a 50 ml volume of stirred 40% ammonium sulfate in 20 mM phosphate buffer that was progressively diluted with ammonium sulfate-free buffer at the same flow rate. Fractions (6 ml) were collected and screened with the micro-plate assay described above and by UV/VIS absorbance (FIG. 1). Positive fractions were pooled, concentrated, and washed in a Centriprep YM-30 centrifuge ultrafiltration device (Millipore, Billerica, Mass., USA) using 20 mM phosphate buffer, pH 7.0, containing 1 mM EDTA.

The concentrated protein (0.3 ml) was then applied to a 0.5×5 cm Source 30S cation exchange column (GE Healthcare, Piscataway, N.J.) equilibrated with 20 mM phosphate buffer, pH 7.0, containing 1 mM EDTA. The column was developed at 0.5 ml/min in a linearly increasing gradient to 1 M KCl in 20 mM phosphate buffer formed by an AKTA-FPLC instrument (GE Healthcare, Piscataway, N.J.). Fractions (0.5 ml) were collected and assessed for purity by UV/VIS spectrum and enzymatic activity. Suitable fractions were combined, concentrated, washed, and stored at −80° C. Final yield of QSOX1 protein from milk varies from approximately 3.3 to 6.6 mg per 100 g protein.

2. Characterization of Milk QSOX1 Protein

Figure 2:
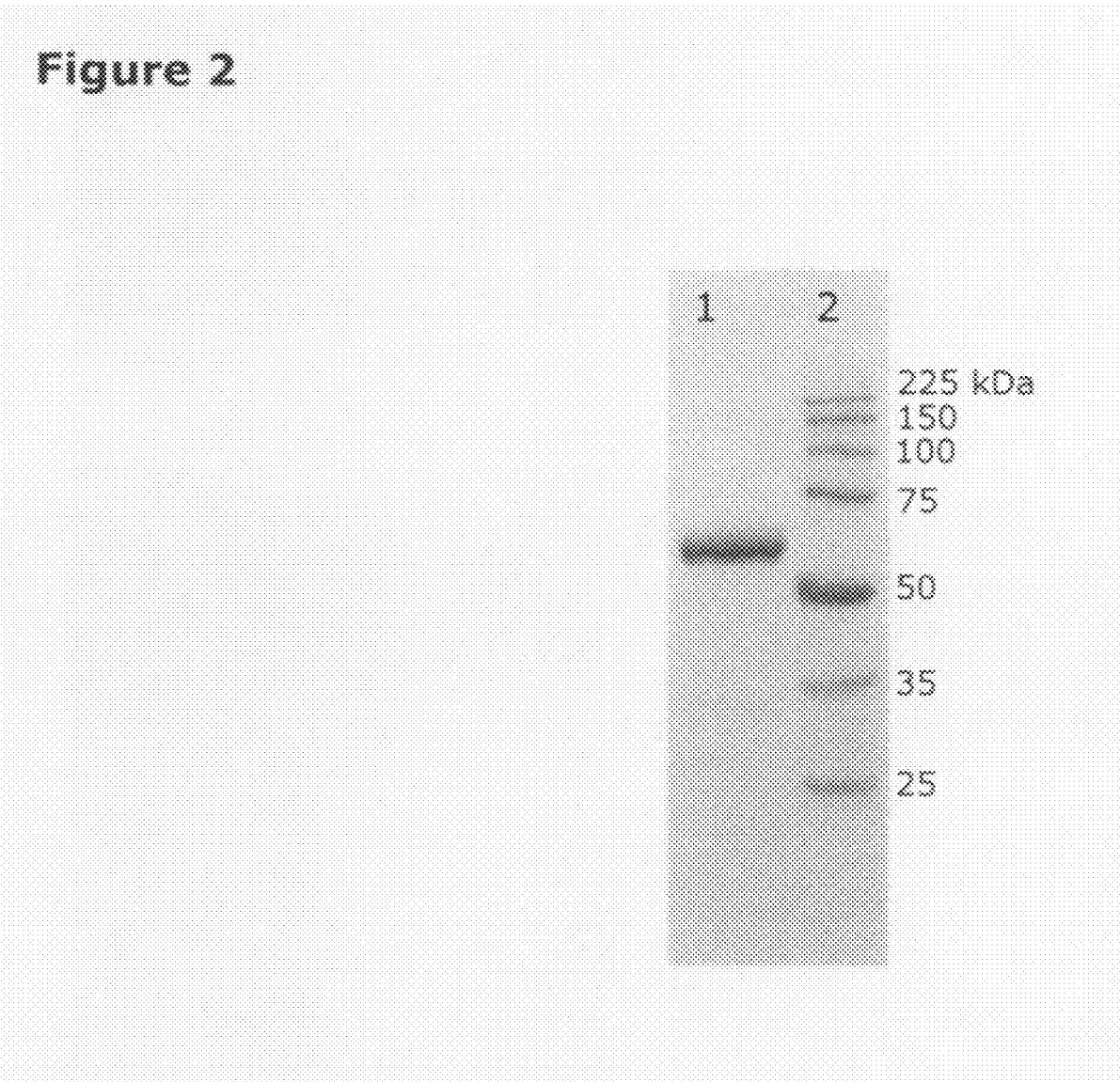
FIG. 2 shows an SDS-PAGE gel of QSOX1 isolated and purified from bovine milk.

The eluted protein exhibited one major band of approximately 62 kD via sodium dodecyl sulfate polyacrylamide gel electrophoresis (SDS-PAGE), FIG. 2.

Coomassie-blue stained protein bands were excised from the SDS-PAGE gels, chopped into 1×1 mm cubes and destained. Gel pieces were then incubated in 10 mM tris-hydroxypropylphosphine/$NH_4HCO_3$ solution for 60 min at 56° C., incubated with a solution of 10 mg iodoacetamide in 1 mL of 100 mM ammonium bicarbonate, washed with 100 mM ammonium bicarbonate, dehydrated and then rehydrated in the minimal volume of a solution of 100 mM ammonium bicarbonate containing 13 micrograms of trypsin/mL to just cover the gel pieces. Excess trypsin was removed by centrifugation, the solution replaced by ammonium bicarbonate alone, and digestion was performed overnight at 37° C.

The resulting peptides were analyzed by LC-MS mass spectrometry using a Micro-Tech Scientific XtremSimple nano-LC system and a Thermo Scientific LTQ mass spectrometer (San Jose, Calif. ). Data was compared against the ipi_BOVIN_v_3_04 database using SageN Sorcer IDA and Thermo Scientific Bioworks 3.3 software. This comparison revealed that the protein was QSOX1. A relatively insignificant amount of heparanase was also identified (average 9,218 QSOX spectra and 122 heparanase spectra per sample).

Figure 3:
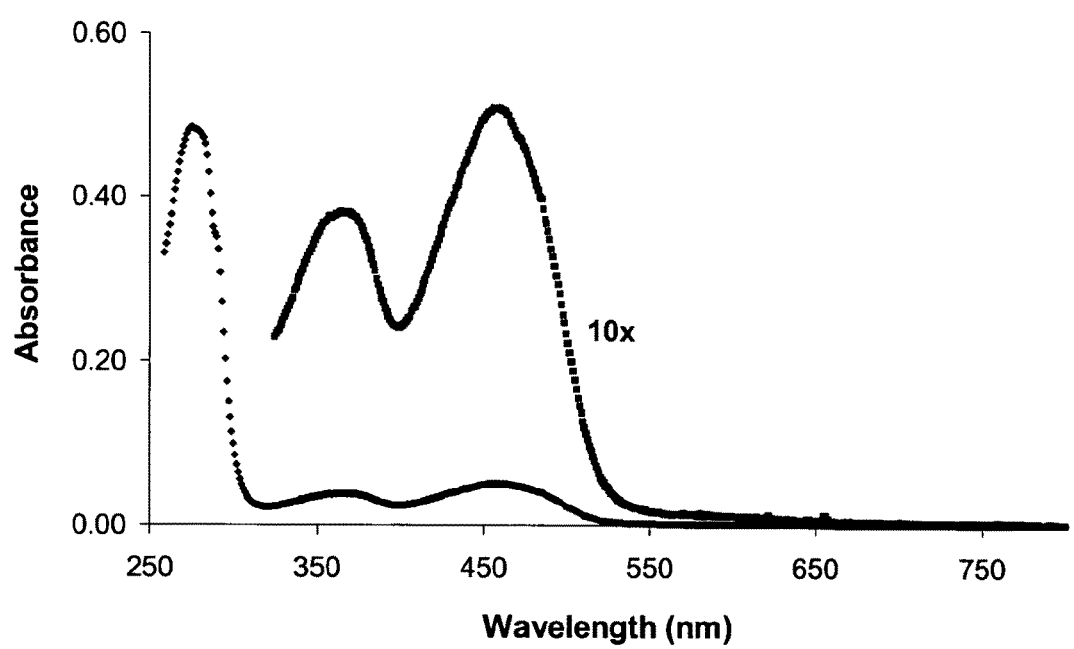
FIG. 3 shows a UV/Vis spectrum of purified milk QSOX1.

Spectra were recorded in 50 mM phosphate buffer, pH 7.5, containing 1 mM EDTA. In FIG. 3, the upper curve is a 10-fold expansion of the lower spectrum in the visible region showing the spectrum of the bound flavin prosthetic group of milk QSOX1 (FIG. 3). The UV/VIS spectrum of fractions from the Source 30S column shows that the purified protein exhibits a flavin spectrum with maxima at 458 and 365 nm, together with a protein absorption envelope contributing to the absorbance at 280 nm (FIG. 3).

3. Oxidative Activity by Bovine Milk QSOX1

A simple, discontinuous screening assay was developed to assay chromatographic fractions. Aliquots of suitable volume (180 μl for CM52 column) were added to 20 μl of 3 mM dithiothreitol (DTT) in the wells of a 96-well plate. The plate was securely covered with parafilm, incubated at room temperature, and quenched after 1 h with 20 μl of 10 mM 5,5'-dithiobis-(2-nitrobenzoic acid) in 50 mM phosphate buffer containing 1 mM EDTA. Absorbance values were recorded with a Perkin Elmer Fusion plate-reader using a 405 nm filter. Peroxidase was also evaluated in 96-well plates by adding 200 μl solution containing 2 mM 4-aminoantipyrene and 20 mM phenol in 20 mM potassium phosphate containing 1 mM EDTA, pH 7.5 to 5 μl protein fractions. The reaction was initiated by adding 10 μl of freshly-prepared 0.3% hydrogen peroxide. Peroxidase-positive wells were recognized by their wine-red color.

Oxygen electrode assays were performed in duplicate at 25° C. as described in K. L. Hoober, et al., *J. Biol. Chem.* 271: 30510-30516, 1996. Assays were initiated by the addition of 5 mM DTT or reduced glutathione (GSH). All thiol substrates were standardized with DTNB before use. Reduced RNase was prepared, characterized and stored as described in K. L. Hoober, et al., *J. Biol. Chem.* 271: 30510-30516, 1996. Assays of the oxidation of reduced RNase were performed as described by K. L. Hoober et al., *J. Biol. Chem.* 274: 22147-22150.

Table 2 shows that the $k_{cat}/K_m$ values for the oxidation of dithiothreitol (DTT), glutathione (GSH) and reduced RNase (rRNase) by bovine QSOX1 from milk are marginally higher than those for avian QSOX1 from egg white and demonstrates that milk QSOX1 is capable of inserting disulfide bonds into reduced proteins.

TABLE 2

Comparison of steady-state catalytic parameters for QSOX1 enzymes isolated from bovine skim milk and avian egg white.[a]

| | Milk QSOX1 | | | Egg QSOX1[b] | | |
|---|---|---|---|---|---|---|
| Substrate | $k_{cat}$ (min$^{-1}$) | $K_M$ (mM) | $k_{cat}/K_M$ (M$^{-1}$s$^{-1}$) | $k_{cat}$ (min$^{-1}$) | $K_M$ (mM) | $k_{cat}/K_M$ (M$^{-1}$s$^{-1}$) |
| DTT | 1880 | 0.086 | 3.66 × 10$^5$ | 2060 | 0.15 | 2.30 × 10$^5$ |
| GSH | 1760 | 4.9 | 5.94 × 10$^3$ | 2780 | 20 | 2.32 × 10$^3$ |
| rRNase | 1340 | 0.060 | 3.74 × 10$^5$ | 1220 | 0.115 | 1.76 × 10$^5$ |

[a]All assays were performed at 25° C. in 50 mM phosphate buffer, pH 7.5, containing 1 mM EDTA. $k_{cat}$ values are expressed as thiols oxidized per minute (to convert to disulfides generated per minute these values should be divided by 2.0).
[b]Data from Hoober, et al., J. Biol. Chem. 274: 22147-22150, 1999, listed as thiols oxidized per minute.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. An isolated and purified QSOX polypeptide having at least 95% identity to the amino acid sequence of SEQ ID NO: 1, wherein the isolated and purified polypeptide is capable of inserting a disulfide bond into a peptide or polypeptide.

2. The isolated and purified QSOX polypeptide of claim 1, wherein the polypeptide consists of a polypeptide having the amino acid sequence of SEQ ID NO:1.

3. A method for isolating and purifying the QSOX polypeptide of claim 1 from milk comprising the steps of
   a) preparing a solution of whey from the milk,
   b) acidifying the solution of whey,
   c) applying the acidified solution of whey to a cation exchanger,
   d) eluting and identifying fractions containing the QSOX polypeptide from the cation exchanger, and
   e) further purifying the QSOX polypeptide in the eluted fractions.

4. The method of claim 3, wherein step e) comprises subjecting the eluted QSOX polypeptide to hydrophobic interaction chromatography.

5. The method of claim 4, further comprising the step of subjecting the QSOX polypeptide to a second cation exchanger, wherein the second cation exchanger has higher column efficiencies for chromatographic polishing than the cation exchanger of step c).

6. The method of claim 3, wherein the isolated QSOX polypeptide is a flavin-dependent quiescin sulfhydryl oxidase.

7. The method of claim 5, wherein the isolated QSOX polypeptide is at least 90% pure.

8. The method of claim 3, wherein the milk is bovine milk.

9. The method of claim 8, wherein the isolated QSOX polypeptide is isolated in quantities of at least 0.27 mg/liter of milk.

10. The method of claim 8, wherein the isolated QSOX polypeptide is isolated in quantities of at least 3.3 mg/100 g whey protein.

11. The method of claim 3 wherein the isolated QSOX polypeptide comprises the amino acid sequence of SEQ ID NO:1.

12. A method for isolating and partially purifying the QSOX polypeptide of claim 1 from a solution of whey comprising the steps of
   a) acidifying the solution of whey,
   b) applying the acidified solution of whey to a cation exchanger,
   c) eluting and identifying fractions containing quiescin sulfhydryl oxidase from the cation exchanger, and
   d) further purifying quiescin sulfhydryl oxidase in the eluted fractions.

13. The method of claim 12, wherein step d) comprises subjecting the isolated QSOX polypeptide to hydrophobic interaction chromatography.

14. The method of claim 13, further comprising the step of subjecting the isolated QSOX polypeptide to a second cation exchanger, wherein the second cation exchanger has higher column efficiencies for chromatographic polishing than the cation exchanger of step b).

15. The method of claim 12, wherein the isolated QSOX polypeptide is a flavin-dependent quiescin sulfhydryl oxidase.

16. The method of claim 14, wherein the isolated quiescin sulfhydryl oxidase is at least 90% pure.

17. The method of claim 12, wherein the whey is bovine whey.

18. The method of claim 17, wherein the isolated QSOX polypeptide is isolated in quantities of at least 3.3 mg/100 g protein from whey.

19. The method of claim 12, wherein the isolated QSOX polypeptide comprises the amino acid sequence of SEQ ID NO:1.

* * * * *